(12) United States Patent
Muellner et al.

(10) Patent No.: US 9,694,152 B2
(45) Date of Patent: Jul. 4, 2017

(54) DEVICE FOR SUPPLYING GAS TO A PATIENT

(75) Inventors: Rainer Muellner, Wiener Neudorf (AT); Christian Romako, Loosdorf (AT); Christian Koehle, Wolkersdorf im Weinviertel (AT)

(73) Assignee: Linde Aktiengesellschaft, Munich (DE)

( * ) Notice: Subject to any disclaimer, the term of this patent is extended or adjusted under 35 U.S.C. 154(b) by 1189 days.

(21) Appl. No.: 13/143,458

(22) PCT Filed: Jan. 7, 2010

(86) PCT No.: PCT/EP2010/000048
§ 371 (c)(1),
(2), (4) Date: Sep. 30, 2011

(87) PCT Pub. No.: WO2010/079134
PCT Pub. Date: Jul. 15, 2010

(65) Prior Publication Data
US 2012/0017908 A1  Jan. 26, 2012

(30) Foreign Application Priority Data
Jan. 8, 2009  (DE) .................. 10 2009 004 107

(51) Int. Cl.
*A61M 16/12*  (2006.01)
*A61M 16/22*  (2006.01)
*A61M 16/00*  (2006.01)

(52) U.S. Cl.
CPC ......... *A61M 16/12* (2013.01); *A61M 16/0078* (2013.01); *A61M 16/22* (2013.01); *A61M 2230/43* (2013.01)

(58) Field of Classification Search
USPC ............ 128/204.18, 204.21–204.23, 204.26, 128/204.28, 205.12–205.18, 205.27,
(Continued)

(56) References Cited

U.S. PATENT DOCUMENTS 3,200,816 A * 8/1965 Bartlett, Jr. .............. 128/204.21
4,879,996 A * 11/1989 Harwood et al. ......... 128/202.26
(Continued)

FOREIGN PATENT DOCUMENTS

DE    9218160 U1   8/1993
DE   19639522 A1   4/1998
(Continued)

OTHER PUBLICATIONS

World IP Organization. "International Search Report and Written Opinion" PCT/EP2010/000048, Applicant: Linde AG, Mailed: May 27, 2010.

*Primary Examiner* — Valerie L Woodward
(74) *Attorney, Agent, or Firm* — Millen White Zelano & Branigan, P.C.

(57) ABSTRACT

The invention relates to a device for supplying gas to a patient, in particular a patient breathing spontaneously. The device includes a) a metering device (A) which is used to meter the gas to be inhaled by the patient (P) into the gas tank (B), b) a gas tank (B) which is used to store the gas to be inhaled by the patient (P), c) a demand valve (D) which regulates the volume flow of the gas inhaled by the patient (P), d) a reservoir (F) which is used to hold the gas exhaled by the patient (P), e) a carbon dioxide separating unit (G) which is used to separate carbon dioxide from the exhaled gas, f) a pump (H) which is used to return the exhaled gas purified of carbon dioxide into the gas tank (B), and g) an analysis/control unit (J) which analyzes the gas returned to the gas tank (B) and controls the metering device (A) according to the composition of said gas.

9 Claims, 1 Drawing Sheet

(58) Field of Classification Search
USPC .................................................. 128/205.28
See application file for complete search history.

(56) References Cited

U.S. PATENT DOCUMENTS

| | | | |
|---|---|---|---|
| 5,810,002 | A | 9/1998 | Dittmann |
| 5,957,129 | A | 9/1999 | Tham et al. |
| 6,123,072 | A * | 9/2000 | Downs ..................... 128/204.21 |
| 6,536,429 | B1 | 3/2003 | Pavlov et al. |
| 7,703,455 | B2 | 4/2010 | Bunke et al. |
| 7,856,978 | B2 | 12/2010 | Dittmann |
| 2001/0022181 | A1* | 9/2001 | Masson et al. .......... 128/203.12 |
| 2003/0131844 | A1* | 7/2003 | Kumar et al. ........... 128/200.24 |
| 2005/0016536 | A1* | 1/2005 | Rapoport et al. ........ 128/204.18 |
| 2005/0103338 | A1 | 5/2005 | Bunke et al. |
| 2006/0090757 | A1 | 5/2006 | Dittmann |
| 2007/0193584 | A1* | 8/2007 | Laurila et al. ........... 128/205.12 |
| 2008/0202526 | A1* | 8/2008 | Heinonen ................ 128/204.22 |
| 2009/0090359 | A1 | 4/2009 | Daviet et al. |
| 2009/0120435 | A1* | 5/2009 | Slessarev et al. ....... 128/203.14 |

FOREIGN PATENT DOCUMENTS

| | | |
|---|---|---|
| DE | 102004052398 B3 | 11/2005 |
| EP | 0861672 A1 | 9/1998 |
| EP | 0894506 A2 | 2/1999 |
| FR | 2862227 A1 | 5/2005 |
| FR | 2894486 A1 | 6/2007 |
| GB | 2368531 A | 5/2002 |

* cited by examiner (A) Metering Device
(B) Gas Storage Unit
(C) Flushing Device
(D) Demand Valve
(E) One-Way Valve
(F) Reservoir
(G) $CO_2$ Separation Unit
(H) Pump
(J) Analysis/Control Unit
(P) Patient
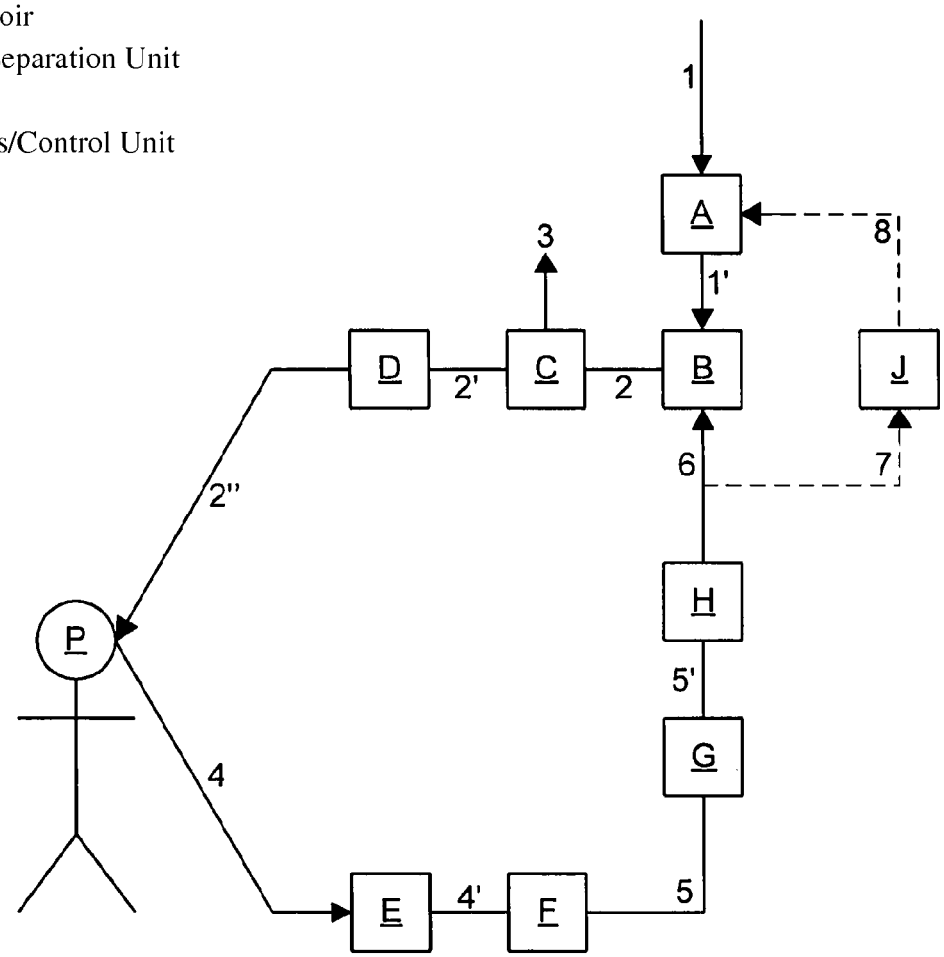

DEVICE FOR SUPPLYING GAS TO A PATIENT

The invention relates to a device for supplying a patient, in particular a spontaneously breathing patient, with a gas.

The term "gas" is defined below as gases and gas mixtures.

Generic devices for supplying a spontaneously breathing patient with a gas are used, for example, in the non-invasive pressure breathing of spontaneously breathing patients by means of the CPAP (Continuous Positive Airway Pressure) method. In this connection, a constant gas flow rate is normally achieved. The flow rate is preset in this case so that the necessary supporting pressure is reached during the inhalation phase as well as the exhalation phase. The supply of the gas to the patient is usually done by means of a nose mask, preferably by means of a face mask. Also, generic devices can be used in intubated patients.

In a number of inhalation treatments, gases are used that either are available only to a limited extent—for example in the case of the preparation of gases by means of compressed gas cylinders—or can be harmful to health in excessive concentrations within the treatment room; this is the case, for example, with laughing gas ($N_2O$). Laughing gas is mixed with oxygen and administered to spontaneously breathing patients for the purpose of analgesic action.

Such treatments are usually practiced in treatment rooms that do not have any systems for suctioning off exhaled gases. Suctioning off gases would prevent exhaled gases from reaching the room and thus increase the gas or workplace concentration in the room beyond the allowable limits.

In addition, it is to be considered that the patient takes only a fraction of the inhaled gases into the body, while a large proportion of the inhaled gases is exhaled unused. This results in that even in the case of a short treatment period, the allowed workplace concentrations can be exceeded.

Another problem arises when using gases that are prepared exclusively in compressed gas cylinders; helium-oxygen mixtures can be mentioned by way of example in this respect. Such gases are comparatively expensive and are not made available by the central gas supply system of the hospital. This means that these gases are available exclusively in compressed gas cylinders of different sizes. In particular, the treatment with helium-oxygen mixtures can last several hours, however. This results in the fact that the gas cylinders very often have to be exchanged during treatment. The logistical effort associated with the exchange of gas cylinders may be considerable. This in turn results in a negative influence on the acceptance of such treatments.

The object of this invention is to indicate a generic device for supplying a patient, in particular a spontaneously breathing patient, with a gas that avoids the previously described drawbacks and in particular makes possible an optimization of the gas consumption with the most varied inhalation treatments of patients with spontaneous respiration. In this connection, treatment parameters, which can influence the compliance of the patient relative to the treatment, such as the inhalative and the exhalative airway resistance, are not to be influenced appreciably.

To achieve this object, a device for supplying a patient with a gas is indicated, which
  a) Has a metering device that serves to meter the gas that is to be inhaled by the patient in the gas storage unit,
  b) A gas storage unit that serves to store the gas to be inhaled by the patient,
  c) A demand valve, which regulates the amount of flow of the gas inhaled by the patient,
  d) A reservoir that serves the purpose of taking up the gas exhaled by the patient,
  e) A carbon dioxide separation unit, which serves to separate carbon dioxide from the exhaled gas,
  f) A pump that serves to recycle the exhaled, carbon-dioxide-purified gas into the gas storage unit, and
  g) An analysis/control unit, which analyzes the gas returned to the gas storage unit and triggers the metering device based on its composition.

Other advantageous configurations of the device according to the invention for supplying a (spontaneously breathing) patient with a gas, which represent subjects of the dependent claims, are characterized in that
  A one-way valve, which prevents the backflow of gas exhaled by the patient, is placed upstream from the reservoir,
  The carbon dioxide separating unit is designed as a carbon dioxide separating unit that operates by absorption, adsorption and/or permeation,
  A flushing device, which serves to drain off gas, is placed upstream from the demand valve,
  The reservoir is designed as a breathing pouch, and
  The pump has a back-up circuit, which prevents the reservoir from being emptied completely.

The device according to the invention for supplying a (spontaneously breathing) patient with a gas as well as further configurations thereof are explained in more detail below based on the embodiment shown in the FIGURE.

The device according to the invention for supplying a (spontaneously breathing) patient with a gas has at least the components mentioned below: a metering device A, a gas storage unit B, a demand valve D, a reservoir F, a carbon dioxide separating unit G, a pump H and an analysis/control unit J. In addition, a one-way valve E and a flushing device C can be provided.

During the inhalation phase, the spontaneously breathing patient P breathes in the required amount of gas, which is prepared in gas storage unit B, via the demand valve D as well as the line sections 2-2". Within the gas storage unit B, an excess pressure of, for example, >500 mbar prevails. The composition of the gas that is prepared in the gas storage unit B has to be kept constant during the treatment period based on the selected type of treatment.

By means of the demand valve D, the excess pressure that prevails within the gas storage unit B is reduced to the inhalation pressure that is determined by the patient P. The amount of gas, which flows through the demand valve D, is controlled by the patient P. Thus, it is ensured that exactly the amount of gas that is required by the patient based on the selected type of treatment can be made available.

The gas exhaled by the patient P is fed via the line sections 4 and 4' to a reservoir F. This reservoir F is preferably designed as a breathing pouch or bag. The composition of the exhaled gas normally differs from the composition of the inhaled gas. The reservoir F serves the purpose of intermediate storage of the exhaled gas. It is preferably designed in such a way that the pressure rises only slightly when the gas volume is increased within the reservoir F. This makes possible a minimal breathing effort for the patient P when exhaling. If the patient P is to be prevented from breathing back from the reservoir F during inhalation, it is recommended that a one-way valve E be connected to the reservoir E. Normally, such a one-way valve E is necessarily to be provided since the patient must not breathe back from the reservoir F.

The gas that is drawn off or removed from the reservoir F is fed via line 5 to a carbon dioxide separating unit G. By means of the latter, the carbon dioxide that is exhaled by the patient P is removed from the gas. The carbon dioxide separating unit G is designed as a separating unit that operates by absorption, adsorption and/or permeation. The supply of the gas removed from the reservoir F via line 5 is carried out by the pump H that is placed downstream from the carbon dioxide separating unit G.

The latter conveys the gas via the line sections 5' and 6 subsequently into the already described gas storage unit B. By means of the pump H, the pressure level is increased from the pressure level of the patient P—the latter near ambient pressure—to the operating pressure level of the previously described demand valve D. By provision of pressure control, the pump H can be turned off when the reservoir F has been emptied.

The composition of the gas pumped back via line 6 is determined by means of the analysis/control unit J—shown in the FIGURE by the line 7 indicated by dotted lines. If the analyzed gas composition does not correspond to the conditions, a triggering of the metering device A is done by the line 8 that is indicated in dotted lines.

The component(s) of the gas prepared in the gas storage unit B, whose content in the determined gas composition is too low, can be added in measured quantities via the line sections 1 and 1' to the gas storage unit B by means of the metering device A. To do this, the metering device A compares the $1^{st}$ concentration with the nominal concentration and uses the calculated deviation to regulate the gas amount(s) that is (are) necessary to achieve the nominal concentration in the gas storage unit B. Thus, the composition of the gas that is breathed in by the patient P can be kept constant. The line 1 is connected or can be connected to a gas source (compressed gas cylinder, liquid tank, central gas supply system of a hospital, etc.) that is arbitrarily designed, not shown in the FIGURE.

In addition, a flushing device C can be provided. Via said flushing device or its drain pipe 3, (excess) gas from the system can be drained off to be able to influence the amount of gas in the gas storage unit B.

With the next breath, the patient P again inhales via the demand valve D the gas (mixture), regulated to the nominal concentration, from the gas storage unit B. The size of the gas storage unit B can be set in such a way that, during inhalation, sufficient gas can always be made available to the patient P.

The device according to the invention for supplying a (spontaneously breathing) patient with a gas has the following advantages relative to the devices that are part of the prior art:

Low airway resistance during inhaling and exhaling
Simplified gas analysis by constant pump flow
Low gas consumption due to a closed circuit; only the gas losses are balanced by means of the metering device
A closed circuit reduces the loading of the environment with breathing gases; it is simpler to adhere to the permissible workplace concentrations
Because of the demand valve, no gas losses when removing the patient mask

The invention claimed is:

1. A device for supplying a spontaneously breathing patient with a gas, the device comprising:
   a) a gas storage unit (B) that serves to prepare and store gas to be inhaled by the patient (P),
   b) a metering device (A) that serves to meter gas that is to be inhaled by a patient (P) into the gas storage unit (B),
   c) a demand valve (D), which regulates the amount of flow of the gas from said gas storage unit (B) inhaled by a patient (P),
   d) a reservoir (F) that serves the purpose of taking up exhaled gas from a patient (P),
   e) a carbon dioxide separation unit (G), which serves to separate carbon dioxide from the exhaled gas,
   f) a pump (H) that serves to recycle exhaled, carbon-dioxide-purified gas to said gas storage unit (B), and
   g) an analysis/control unit (J), which analyzes the exhaled, carbon dioxide purified gas recycled to said gas storage unit (B) and controls said metering device (A) for monitoring gas to be inhaled into said gas storage unit (B) based on the composition of analyzed carbon dioxide purified gas.

2. The device according to claim 1, wherein a one-way valve (E), which prevents backflow of gas exhaled by a patient (P), is placed upstream from the reservoir (F).

3. The device according to claim 2, wherein the carbon dioxide separating unit (G) operates by absorption, adsorption and/or permeation.

4. The device according to claim 1, wherein a flushing device (C), which serves to drain off gas, is placed upstream from the demand valve (D) and downstream from said gas storage unit (B).

5. The device according to claim 1, wherein the reservoir (F) is designed as a breathing pouch.

6. The device of claim 1 wherein a pressure controller acts to turn off the pump H when the reservoir (F) has been emptied.

7. The device of claim 1 wherein the carbon dioxide separation unit (G) receives gas from the reservoir (F).

8. The device of claim 7 wherein the pump (H) moves gas from the reservoir (F) to the gas storage unit (B) and the analysis/control unit (J) analyses the composition of gas flowing from the carbon dioxide separation unit (G) to the gas storage unit (B).

9. The device of claim 1 wherein the pump (H) moves gas from the reservoir (F) to the gas storage unit (B) and the analysis/control unit (J) analyses the composition of gas flowing from the reservoir (F) to the gas storage unit (B).

* * * * *